United States Patent
Bavendiek

(10) Patent No.: US 9,322,936 B2
(45) Date of Patent: Apr. 26, 2016

(54) X-RAY LINE DETECTOR

(71) Applicant: Yxlon International GmbH, Hamburg (DE)

(72) Inventor: Klaus Bavendiek, Norderstedt (DE)

(73) Assignee: Yxlon International GmbH, Hamburg (DE)

( * ) Notice: Subject to any disclaimer, the term of this patent is extended or adjusted under 35 U.S.C. 154(b) by 269 days.

(21) Appl. No.: 14/141,628

(22) Filed: Dec. 27, 2013

(65) Prior Publication Data

US 2014/0183370 A1    Jul. 3, 2014

Related U.S. Application Data

(63) Continuation of application No. 13/988,030, filed as application No. PCT/EP2011/005826 on Nov. 18, 2011, now abandoned.

(30) Foreign Application Priority Data

Nov. 18, 2010 (DE) .......................... 10 2010 051 774

(51) Int. Cl.
*G01B 15/06* (2006.01)
*G01T 1/20* (2006.01)
*G01N 23/18* (2006.01)

(52) U.S. Cl.
CPC ............ *G01T 1/2018* (2013.01); *G01N 23/185* (2013.01); *G01N 2223/627* (2013.01)

(58) Field of Classification Search
CPC .......... G01N 2223/627; G01N 23/185; G01N 23/043; G01N 23/04; G01M 17/028
USPC ............................................ 250/366; 378/61
See application file for complete search history.

(56) References Cited

U.S. PATENT DOCUMENTS

| | | | | |
|---|---|---|---|---|
| 5,148,456 A | * | 9/1992 | Steffel | G01M 17/028 250/370.09 |
| 5,737,383 A | * | 4/1998 | Noda | G01M 17/028 378/57 |
| 8,124,938 B1 | * | 2/2012 | Tseng | H01L 27/14618 250/208.1 |
| 2005/0175146 A1 | * | 8/2005 | Uchida | G01N 23/04 378/61 |
| 2012/0148024 A1 | * | 6/2012 | Suyama | G01V 5/005 378/62 |

* cited by examiner

*Primary Examiner* — David J Makiya
*Assistant Examiner* — Kenneth J Malkowski
(74) *Attorney, Agent, or Firm* — Leydig, Voit & Mayer, Ltd.

(57) ABSTRACT

An X-ray line detector includes a housing having an upper part a lower part and a linear inlet slot for X-ray radiation to be detected. At least one detector element including a plurality of linearly arranged photodiodes is disposed opposite the inlet slot. Each photodiode is arranged on a printed circuit board mounted on a base carrier disposed in the housing. Each photodiode has a multiplicity of pixels including respective active areas of equal width arranged equidistantly in relation to each other with distances between the active areas being equidistant. Adjacent printed circuit boards are spaced apart from each other at a distance such that edge pixels on the respective adjacent printed circuit boards are disposed at a distance from one another corresponding to a sum of the width of the active area of a pixel and twice the distance between adjacent pixels of a photodiode.

23 Claims, 9 Drawing Sheets

X-RAY LINE DETECTOR

CROSS REFERENCE TO RELATED APPLICATIONS

This application is a continuation application from U.S. patent application Ser. No. 13/988,030, which is a National Phase application under 35 U.S.C. §371 of International Application No. PCT/EP2011/005826, filed on Nov. 18, 2011, which claims benefit to German Patent Application No. DE 10 2010 051 774.7 filed on Nov. 18, 2010. The International Application was published in German on May 24, 2012, as WO 2012/065752 A2 under PCT Article 21 (2). The entire disclosure of the International Application and of German Patent Application is incorporated by reference herein.

FIELD

The invention relates to an X-ray line detector having at least one detector element with a plurality of linearly arranged photodiodes which are arranged in each case on a printed circuit board, which printed circuit boards are mounted on a base carrier, wherein each photodiode has a multiplicity of pixels of equal width, arranged equidistantly in relation to each other, and having a housing, in which the base carrier is arranged, wherein the housing has a linear inlet slot for the X-ray radiation to be detected, opposite which inlet slot the photodiodes are located.

BACKGROUND

In the examination of tyres, by means of X-ray radiation, for production faults, an X-ray line detector is used which has the shape of a horseshoe, thus is U-shaped in top view. Aligned inwardly along the course of the horseshoe there is an inlet slot which extends over the entire horseshoe and behind which photodiodes detect a fan-shaped X-ray beam, after the latter has passed through the tyre and been converted by a scintillator. The exact positioning of the photodiodes behind the inlet slot is an operation that, in situ, is mechanically very elaborate and time-intensive, wherein an iterative procedure is normally required for the fine adjustment. The photodiodes located on a printed circuit board—of which a plurality are arranged next to each other—have a multiplicity of individual pixels. The individual pixels are in each case connected to a multiplexer via an electrical line. From the multiplexer, the data originating from the individual pixels are forwarded, via a data line, to an A/D converter, located outside of the X-ray line detector on a separate printed circuit board. In this case, usually only one single A/D converter is used for the data from many or all photodiodes. The then digitized data are processed, by means of methods known to a person skilled in the art, and finally converted into an image of the screened tyre, which can be viewed on the monitor screen by an operator. On the basis of this image, the operator then decides whether the tyre is defective.

On the one hand, such an X-ray line detector is mechanically complex in its structure, since many components are needed in order to achieve the fine adjustment of the individual photodiodes in relation to each other so as to obtain an image that has informative value for the operator. Moreover, such an X-ray line detector is also disadvantageous in respect of the electronics, since the image quality is not particularly good, owing to interfering signals and distortions.

SUMMARY

In an embodiment, the present invention provides an X-ray line detector includes a housing having an upper part a lower part and a linear inlet slot for X-ray radiation to be detected. At least one detector element including a plurality of linearly arranged photodiodes is disposed opposite the inlet slot. Each photodiode is arranged on a printed circuit board mounted on a base carrier disposed in the housing. Each photodiode has a multiplicity of pixels including respective active areas of equal width arranged equidistantly in relation to each other with distances between the active areas being equidistant. Adjacent printed circuit boards are spaced apart from each other at a distance such that edge pixels on the respective adjacent printed circuit boards are disposed at a distance from one another corresponding to a sum of the width of the active area of a pixel and twice the distance between adjacent pixels of a photodiode.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
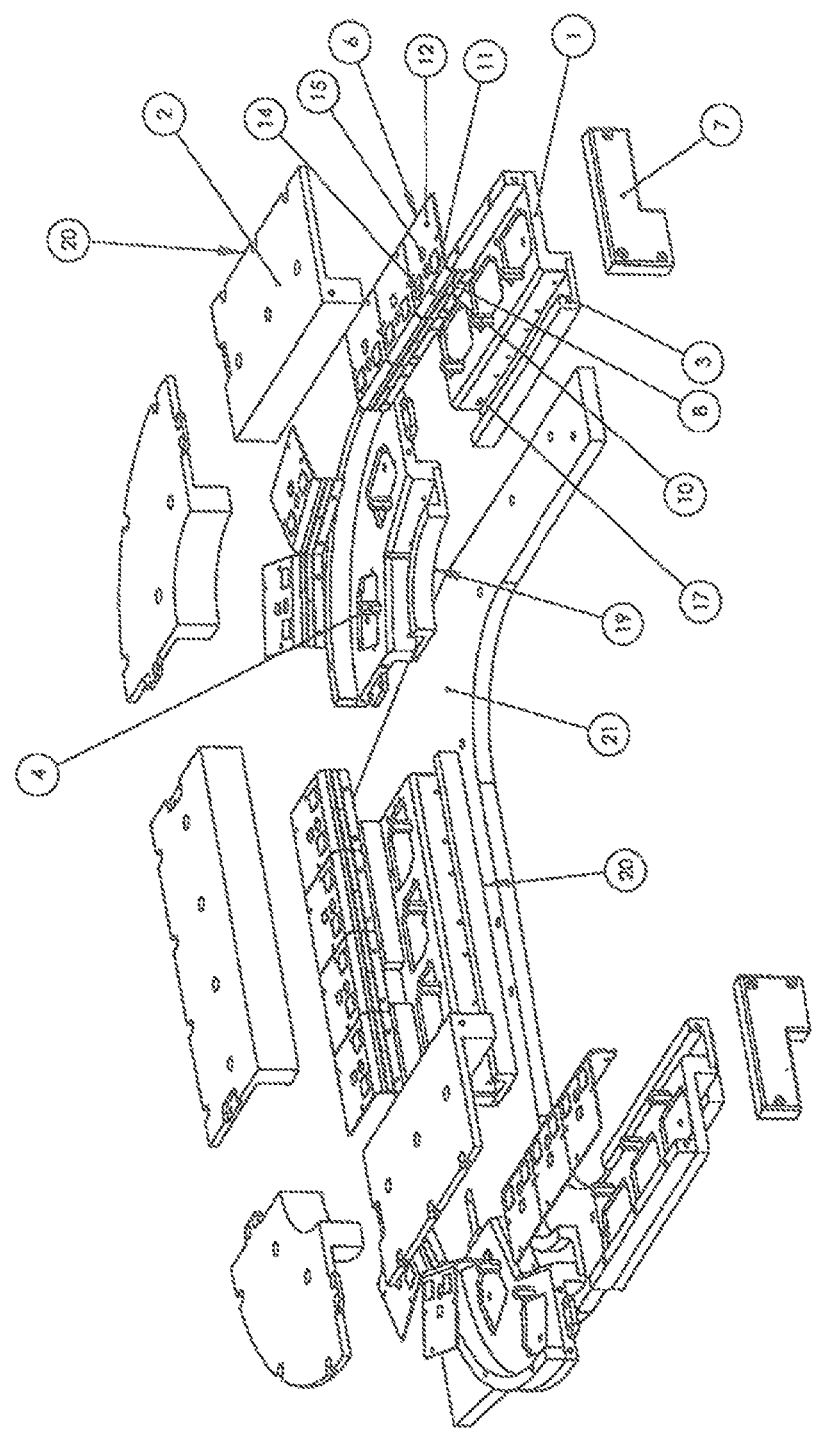
FIG. 1 shows an exploded drawing with the essential elements for an X-ray line detector according to the invention.

An aspect of the invention is to provide an X-ray line detector that makes possible a mechanically simpler structure with, at the same time, a high degree of precision in the arrangement of the photodiodes in relation to each other and, in addition, also results in an improved image quality.

In an embodiment of the present invention an increase in the image quality, as compared with the state of the art, is achieved in that the distance between two photodiodes that are arranged on adjacent printed circuit boards is set and the photodiodes are mechanically fixed onto the base carrier such that the distance between the adjacent pixels of the one and of the other photodiode is just as great as would be the case if the two photodiodes were a single photodiode and only one pixel were omitted therefrom. The photodiodes have in each case the same pixel width and the same distance between two pixels, with the result that the set distance is the sum of the width of one pixel and twice the distance between two adjacent pixels. As a result, in the monitor-screen representation used by the operator for assessing whether a tyre is defective, it is possible to take the region between the two edge pixels of the mutually abutting printed circuit boards from a simple interpolation of the greyscale values of the two adjacent pixels at the edge of the mutually abutting photodiodes, for example by taking the mean value between the two grey levels. Reference could also be made to a "virtual pixel", which is simply filled by the interpolated value. Consequently, there are no defects in the screening image that is obtained, since an equidistant division—as is also the case within a photodiode, between adjacent pixels—is achieved. Thus, for example, wires in an examined tyre do not appear as cut off, but are represented as continuous. This makes it considerably easier for the operator to make an assessment, on the basis of the screening image represented on the monitor screen, of whether the tyre or object then undergoing examination is defective.

In an embodiment, the present invention provides an X-ray line detector where the upper part, the lower part and the base carrier consist of the same material, such that it is ensured that in the case of temperature fluctuations no differing expansions result, which would result in mechanical stresses that would adversely affect the high precision of the alignment of the photodiodes and in the X-ray image. Moreover, also no contact potentials then form, owing to the difference in position in the electrochemical series. Approximately the same effects can be achieved if the materials used, although not identical, are close to each other in respect of their coefficients of thermal expansion and their position in the electrochemical series in each case. In the context of this application, by close to each other is meant that the difference in the linear coefficient of thermal expansion is less than ±4.5*10-6/K at 20° C. and, in the standard potential, is less than ±0.2 V. Preferably, it is not only the above-mentioned parts that are constituted thus, but all parts consisting of a metal, in particular also the precision screws and the spacer screws.

In an other embodiment, the present invention provides an X-ray line detector in which in relation to the first part, to which the photodiodes are attached, the remainder of the printed circuit board is bent away, the further electronic devices arranged on the printed circuit board, which are very sensitive to X-ray radiation, can be taken out of the beam path of the X-ray radiation to be detected. Moreover, owing to the bent structure of the printed circuit board, it is possible to achieve a very narrow design in respect of the extent perpendicular to the inlet slot, with the result that fewer distortions occur in the image of the object, in particular a tyre, to be examined Finally, because of such a bent structure, a higher signal-to-noise ratio is also obtained, since, owing to the continuous lines, fewer contacts—i.e. transitions—are required in comparison with a solution consisting of two boards connected via contacts.

An advantageous development of the invention provides that the upper part and the lower part, between which the inlet slot is formed, and the base carrier are spatially matched to each other such that the base carrier serves as a shielding for the second region, which adjoins the bend region and faces away from the first region, against the X-ray radiation which forms as a result of scattering within the detector element. The sensitive electronic devices already described above are thereby even better protected against X-ray radiation, including scattered radiation. This results in yet further improvement of the functioning of the X-ray line detector. Since the base carrier is usually made from a steel or non-ferrous metal, it has sufficiently good shielding of the X-ray radiation.

A further advantageous development of the invention provides that the part of the upper part that faces towards the X-ray radiation, in dependence on the material used therefor, is formed so thick that electronic components arranged on the printed circuit board, in a second part of the printed circuit board behind the bend region, are protected against direct X-ray radiation. It is therefore not necessary to attach additional shielding devices, made of lead, in the direct X-ray beam, which is more environmentally friendly and, moreover, avoids the need for a considerable amount of additional mechanical outlay. Since the upper part is usually made from a steel or non-ferrous metal, it has a sufficiently good shielding of the X-ray radiation when adequately dimensioned.

A further advantageous development of the invention provides that the X-ray line detector has a combination of at least two of the following designs: bent printed circuit board according to claim 3; identical or similar material of the named parts according to claim 2; precisely defined "virtual pixel" between two adjacent printed circuit boards according to claim 1. The advantages named above in relation to the respective claims are thereby cumulated.

An advantageous development of the invention provides that attached to each printed circuit board there are in each case at least two photodiodes, wherein the distance thereof in relation to each other is selected such that the centre of the last edge pixel of a photodiode is twice the distance of the effective pixel size to the centre of the first edge pixel of the adjoining photodiode. As a result, the printed circuit board becomes so wide that two multiplexers—one for each photodiode—together with an additional A/D converter and a control logic system can be accommodated on this printed circuit board without the need for long line lengths or additional contacts. Consequently, interfering signals and distortions of the image are suppressed, since, for the analogue signals, each contact point—which is avoided by this—involves contact resistances and reflections. Non-uniform pixel distances result in discontinuities in the image, particularly at the edge pixels. The possibility of also attaching to each printed circuit board an A/D converter that has to "serve" only two multiplexers, and therefore two photodiodes, increases the scanning speed of the X-ray line detector. Owing to the short line paths from the multiplexer to the A/D converter, the line capacitances are also reduced, with the result that rapid reloading to new signal levels is also made possible for the edge pixels.

A further advantageous development of the invention provides that the electronic components are arranged, for the purpose of reading out the signals coming from the pixels, such that there is a centre-symmetrical arrangement in relation to the two photodiodes and, consequently, symmetrical read-out is made possible. Owing to the symmetrical read-out, no signal level fluctuations are obtained, since any fluctuations cancel each other out.

A further advantageous development of the invention provides that, for each photodiode, a multiplexer is arranged on the printed circuit board and this/these multiplexer(s) is/are directly connected to an A/D converter, which is also arranged on the printed circuit board. As has already been stated above, an increased read-out speed is thereby achieved, since one A/D converter is responsible for just two photodiodes, and no longer for a plurality or all of them, as was the case in the state of the art. Owing to the local proximity between multiplexer and A/D converter, only small parasitic capacitances result. Edge pixels, the signal of which hitherto was slurred because of the long lines to the A/D converter board, can now be used fully; an interpolation, as required hitherto, need no longer be effected. Finally, owing to the digitizing of the read-out data of the photodiode, sensitivity to interferences is reduced already on the printed circuit board.

A further advantageous development of the invention provides that the analogue components are arranged on one side of the printed circuit board and the digital components are arranged on the other side of the printed circuit board. As a result, it is possible that the electric power supply can be routed separately on differing sides, no interfering capacitances come into play via the printed circuit board, and a clear separation is achieved between the signal paths for the analogue signals and the digital signals.

A further advantageous development of the invention provides that between each printed circuit board and the base carrier at least one contact region is present as a thermal bridge, wherein the base carrier has a material of good thermal conductivity, for example a metal, which is connected to the thermal bridge. As a result, it is not necessary to provide additional cooling elements for the electronic devices, which results in better heat transfer and in a simpler mechanical structure. Particularly preferably, the thermal bridge connects the analogue components to the base carrier.

A further advantageous development of the invention provides that arranged between the upper part and the base carrier there is a distance-changing device, in particular spacer screws. This makes it possible to vary the width of the inlet slot and to set it to the optimum value respectively required in the individual case.

A further advantageous development of the invention provides that the base carrier and the lower part are formed as one piece. The mechanical stability of this combined part is thereby increased.

A further advantageous development of the invention provides that suitable apertures, in particular through-holes, or a suitable mounting, are formed in the lower part for the purpose of fastening the printed circuit boards. This enables the printed circuit boards to be easily fastened to the base carrier, even in the case of the single-piece, combined part.

A further advantageous development of the invention provides that the upper part and/or the lower part, each taken by itself, is/are formed as one piece over the entire X-ray line detector. For a non-modular structure, this achieves a very good mechanical stability, which improves the constancy of the width of the inlet slot. In addition, the lower part, which in this case is U-shaped, can also be formed as one piece with the base carrier, which is likewise U-shaped in this case.

A further advantageous development of the invention provides that each printed circuit board is aligned with high precision in relation to the base body by means of at least one precision screw screwed into a fastening hole in the base body. As a result, the exact distances, already stated above, between two adjacent printed circuit boards, and therefore for the "virtual pixel", can be set in a very simple manner. In this case, it is only necessary to connect the respective printed circuit board to the base body by means of the precision screw. Further adjustment tasks—in particular the high-grade, elaborate fine adjustment according to the state of the art, with iterative steps—are not required.

A further advantageous development of the invention provides that the distances of the fastening holes in the base body that are respectively assigned to the left through-hole of a printed circuit board follow the formula: $(n+1)*PS*$(number of photodiodes per printed circuit board), wherein n is the number of pixels per photodiode and PS is the effective pixel size. This ensures that the printed circuit boards are aligned with high precision in relation to each other, wherein precisely one "virtual pixel" remains free between mutually adjoining printed circuit boards. This applies irrespective of the actual width of a printed circuit board, which width normally has a variation of up to 150 µm, which is in a range that is greater than the distance between two pixels of a photodiode.

A further advantageous development of the invention provides that the precision screw has a conically formed screw head, in particular that it is a countersunk screw. As a result, a very precise alignment of the printed circuit board on the base body is achieved, owing to the centring effect of the conical screw head in the through-hole of the printed circuit board. In the context of this application, by a precision screw is meant any screw that, by acting in combination with the through-hole in the printed circuit board and the fastening hole in the base carrier, is able to effect high-precision alignment and fixing of the printed circuit board on the base carrier and in relation to the other printed circuit boards. This can also be a screw customary in the trade.

A further advantageous development of the invention provides that the X-ray line detector has at least two detector elements according to the invention, wherein these detector elements are connected to each other either directly or via curved detector elements, with the result that the X-ray line detector has a rectilinear shape or an L shape or a U shape. Owing to the fact that the profile of the tyres is U-shaped in cross section, the U shape is advantageous for tyre inspection, since this results in the smallest possible distortions resulting from the imaging geometry. In addition, it is thereby ensured that a modular structural form is possible, which relates to the various sizes of tyres to be examined, by insertion of one or more straight detector elements at the required location—whether in both limbs of the U shape or in the base thereof. In principle, therefore, each limb or the base of the U shape can in each case be lengthened or shortened by one printed circuit board or by a whole-number multiple thereof.

Represented in FIG. 1 is an exploded drawing of an X-ray line detector according to the invention, which has a horseshoe shape or is U-shaped. The figure does not show all individual parts that belong to the X-ray line detector, but only those that are of major relevance to the invention.

The X-ray line detector is composed of five constituent parts, three straight detector elements 20 (which form the two limbs of the U-shaped X-ray line detector and the base thereof), and curved detector elements 19 that connect the latter detector elements together. The individual straight detector elements 20 and the curved detector elements 19 have the same basic structure, wherein the sole fundamental difference is that the straight detector elements 20 have X-ray line modules 6 arranged parallelwise in relation to each other, whereas these X-ray line modules 6 are arranged at an angle in relation to each other in the case of the curved detector elements 19. The two straight detector elements 20 that form the two limbs of the X-ray line detector each have, for example, three X-ray line modules 6, and the base of the X-ray line detector has, for example, four printed circuit boards 6.

The structure of a straight detector element 20 according to the invention is described in more detail in the following on the basis of the limb of the straight detector element 20 represented on the right in the drawing. The other straight detector elements 20 and the curved detector elements 19 are substantially the same in their structure.

Figure 2:
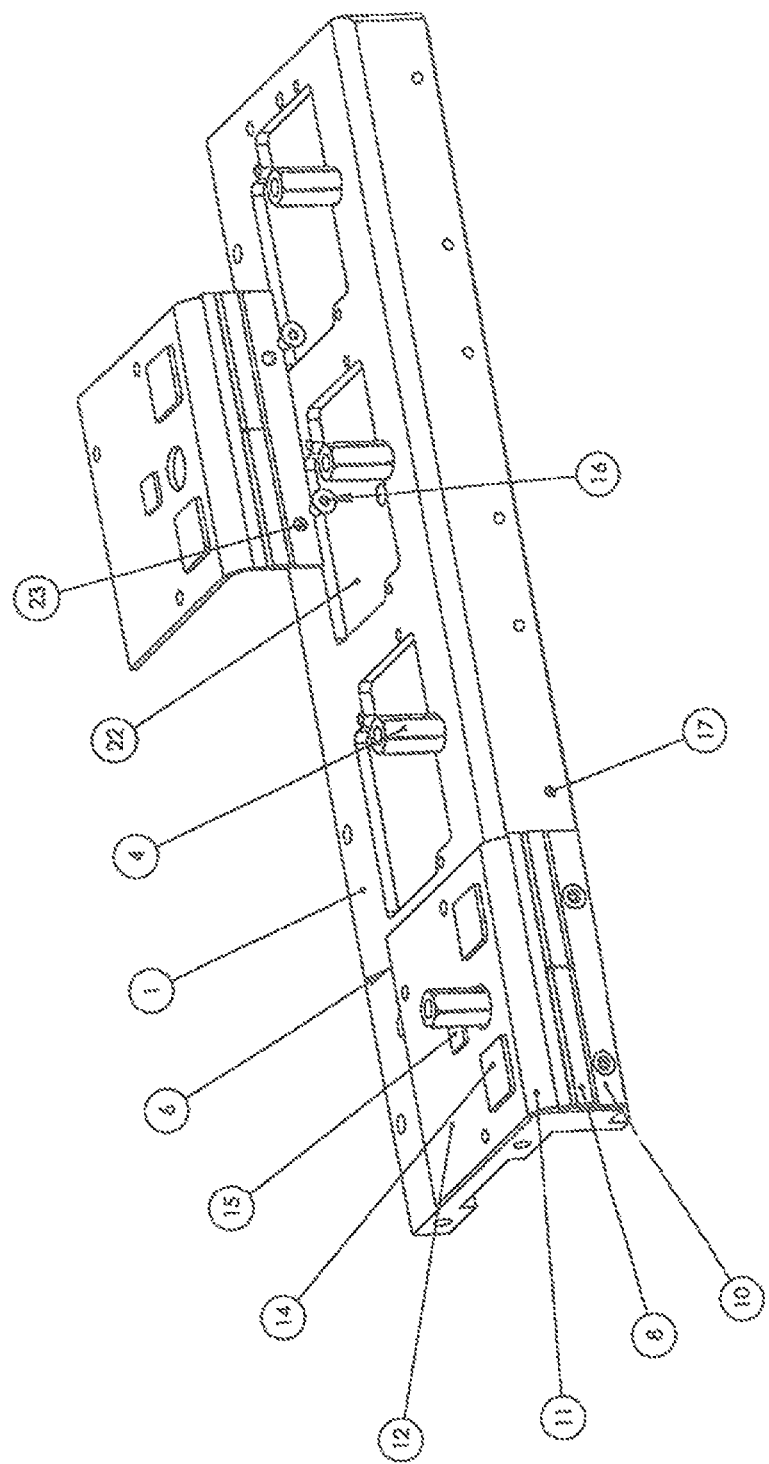
FIG. 2 shows a schematic view of a base carrier with, in part, printed circuit boards already attached thereto.
Figure 3:
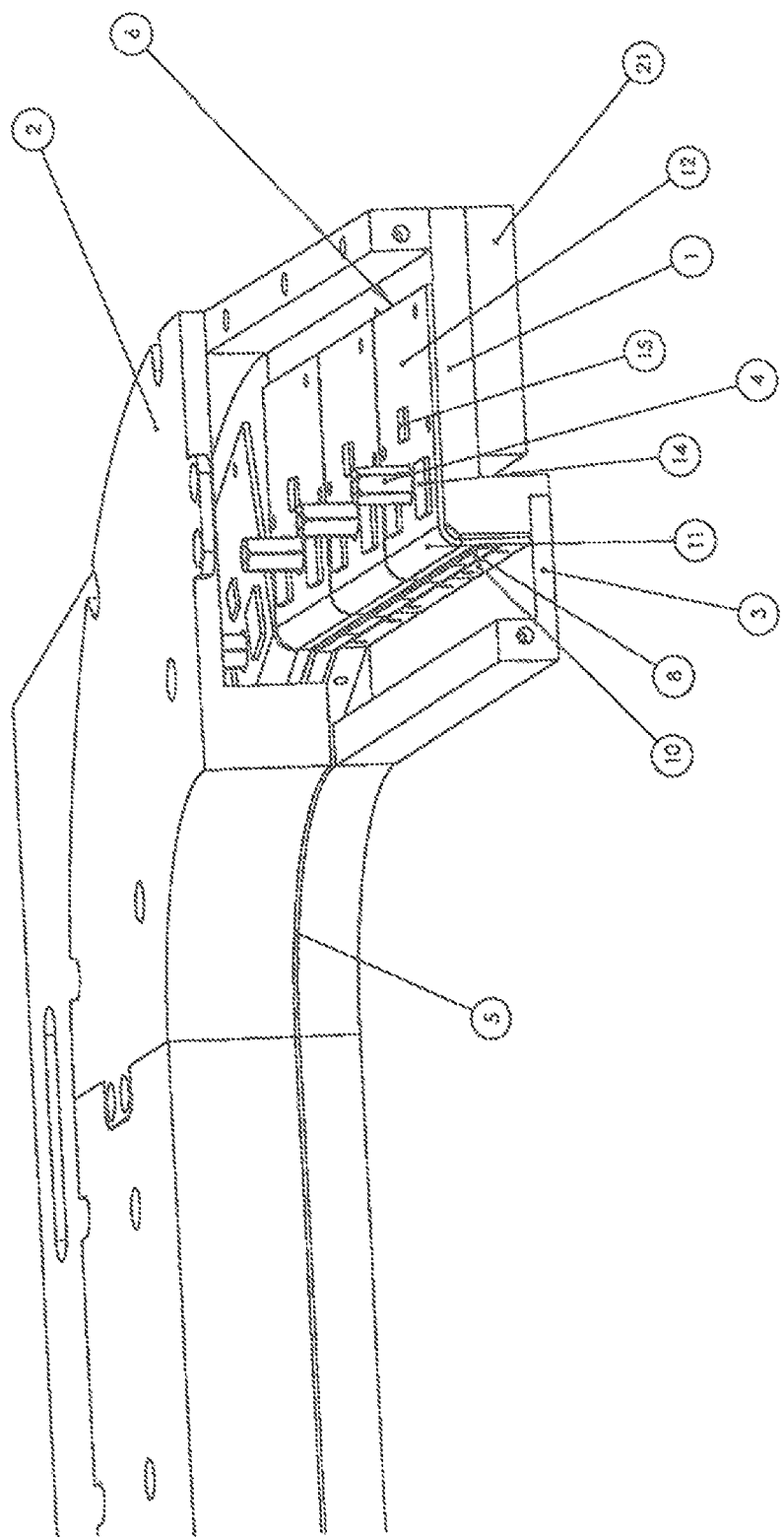
FIG. 3 shows a schematic view in which the upper part of the housing has been partially omitted.

The straight detector element 20 has a base carrier 1, which is formed substantially L-shaped in lateral cross section (as viewed from front right in FIG. 3). Its front, vertically extending wall is adjoined at the bottom, forwardly projecting, by a lower part 3, which is connected with the upper part 2 to the base carrier 1 by means of spacer screws 4 (see FIGS. 2-4) such that the distance between the upper part 2 and the base carrier 1 can be altered. An inlet slot 5 (see FIG. 4) is formed in the front region, between the upper part 2 and the lower part 3.

The part of the base carrier 1 that extends horizontally on the right contains three openings 22 (see FIG. 2), which receive electronic components that are located on the bottom of a printed circuit board 6.

In the vertically extending front part of the base carrier 1 there are formed a total of six screw holes 17, into which precision screws 16 (see FIGS. 2 and 3) can be screwed, for the purpose of precisely aligning and fixing the printed circuit board 6 on the base carrier 1.

Figure 4:
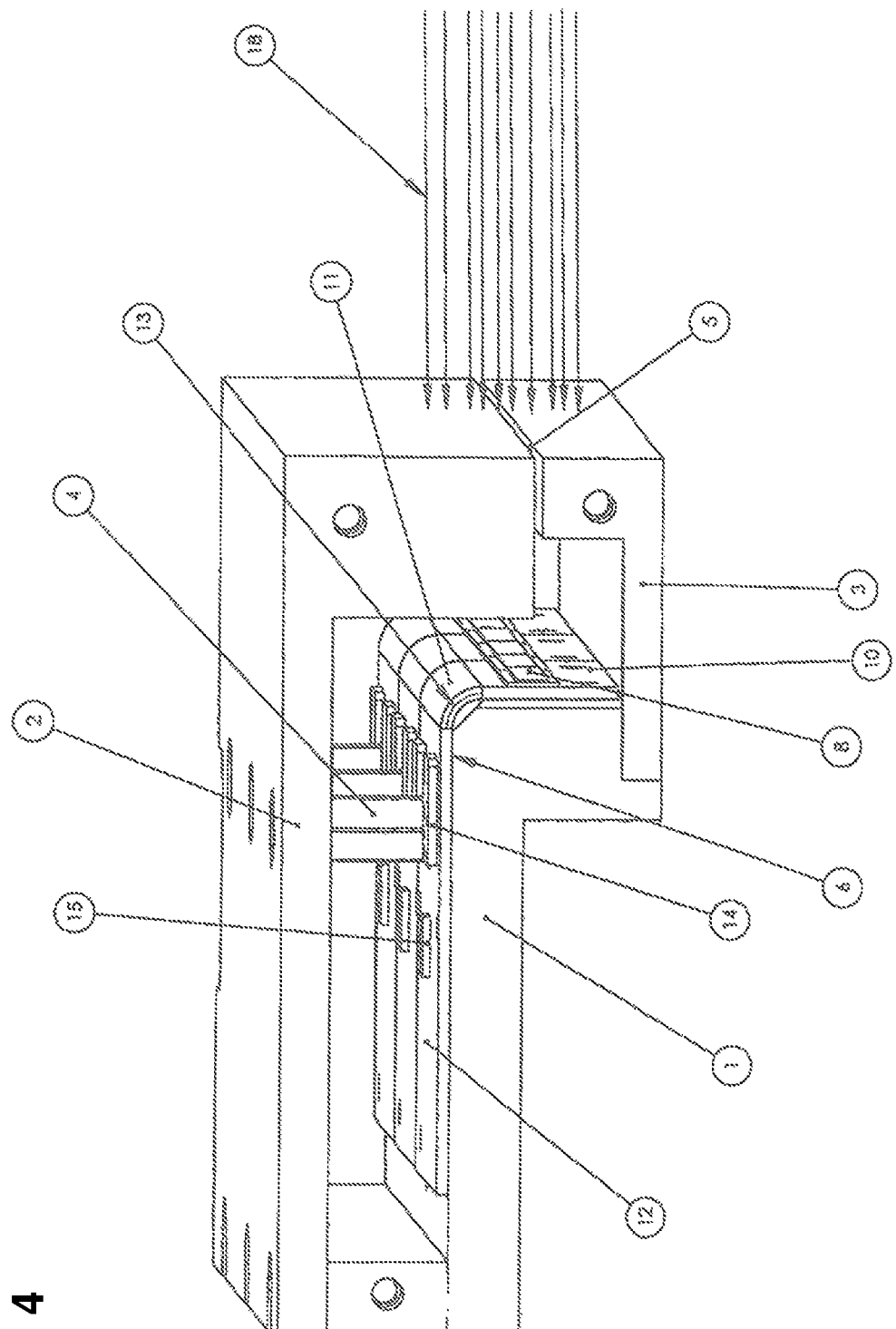
FIG. 4 shows an oblique side view of a mounted detector line element with incident X-ray radiation.

Both the lower part 3 and the upper part 2 each have an L shape, wherein the mutually opposite limbs—as already stated above and represented in FIG. 4-form an inlet slot 5, which is adjustable in its height and through which X-ray radiation 18 enters the detector element 20. The X-ray radiation 18 in this case, starting from an X-ray source, has screened the test object to be examined—for example a tyre—and, on the basis of the intensity distribution of the X-ray radiation, an inference can be drawn concerning the quality of the examined object (further statements relating to this follow below).

The three parts, base carrier 1, upper part 2 and lower part 3, are preferably made of a steel alloy. Other materials that shield against X-ray radiation can likewise be used, provided that they ensure that the overall structure remains stable.

Three printed circuit boards 6 are screwed onto the base carrier 1. Each of the three printed circuit boards 6 has three regions, wherein a first part 10 and a second part 12 are formed rigid and can be bent in relation to each other by means of a bend region 11, in the form of a flexible printed circuit board film, arranged between and connected as one piece to these two parts 10, 12. In the region of the first part 10 there are two through-holes 23, positioned with high precision, for receiving the precision screws 16 (see FIG. 2) by which the printed circuit boards 6 are aligned with high precision on the base carrier 1.

Two photodiodes 8 are arranged next to each other in the region of the first part 10. Each photodiode 8 has a predefined number n of pixels 9 and edge pixels 9' (see FIG. 5), which are of equal width and arranged equidistantly in relation to each other. The exact design of the photodiodes 8 is discussed in yet more detail below.

When in the final mounted state, the totality of pixels 9 of all photodiodes 8 used thus form a U-shaped X-ray line detector. Each pixel 9 transmits the converted X-ray radiation 18, via in each case an electrical line 13 (see FIG. 4), to a multiplexer 14, which is located on the second part 12 of the printed circuit board 6. Each photodiode 8 in this case has its own assigned multiplexer 14. The electrical lines between pixel 9 and multiplexer 14 are connected continuously, with the result that there is no need for plug connectors, which could give rise to interferences. Arranged on the printed circuit board 6, in immediate spatial proximity to the two multiplexers 14, there is an A/D converter 15, which is connected to these two multiplexers. Because of the very short transmission paths from the multiplexers 14 to the A/D converter 15, only small parasitic capacitances result. All analogue electronic components are arranged on the top side of the second part 12 of the printed circuit board 6, whereas the digital electronic components are arranged on the underside of the printed circuit board 6. These digital electronic components are received by an opening 22 (see FIG. 2) in the top side of the base carrier 1. This opening 22 is designed—particularly in its depth—such that a thermal bridge is formed between these components and the base carrier 1, to enable the heat produced in these components to be better dissipated. The cooling of the analogue components is achieved in that, for the latter, the heat is dissipated by the base carrier 1 via metal regions extending through to the underside of the printed circuit board 6. The signals received by the photodiodes 8 are then processed, by means of devices and methods known to a person skilled in the art, such that they are displayed on a monitor screen for an operator, and the latter can assess whether the object to be examined is defective. Since these designs and methods are not essential to the invention and are well known to a person skilled in the art, they are not described in more detail here.

The individual parts (straight detector elements 20 and curved detector elements 19) are connected to each other, by means of suitable connection methods known to a person skilled in the art, such that they are fully positionally stable in relation to each other. This is necessary in respect of a good quality of the screening image of the test object, since the system must have precise knowledge of the exact screening geometry, from the X-ray source to the individual pixels 9.

The complete X-ray line detector, composed of the individual parts just mentioned, is therefore constructed as a kind of U-shaped tube. Attached at each of its two ends there is in each case an end wall 7, which is substantially L-shaped in top view. This serves to seal off the electronic devices inside the X-ray line detector, which are highly sensitive, from all environmental influences. The open inlet slot 5 is closed by a thin, slightly absorptive metal foil.

FIG. 2 shows clearly how the individual structural elements are arranged in relation to each other on the printed circuit boards 6 and how these printed circuit boards 6 are attached to the base carrier 1. For the purpose of locating and fixing each individual printed circuit board 6 with high precision, the base carrier 1, in the region of its vertically extending front face, for each printed circuit board 6, has two screw holes 17 into which a precision screw 16 is screwed in each case. The precision screws 16 engage in each case through a through-hole 23 in the printed circuit board 6. This makes it possible for the photodiodes 6, with their pixels 9, to be located with high precision at the desired location. Particularly with regard to the distance between two adjacent printed circuit boards 6, it is essentially important, for the quality of the representation of the screened object on the monitor screen, that the predefined distance between the two printed circuit boards 6 is also realized in practice, and that this does not alter. This is explained in more detail below with reference to FIGS. 5 and 6. Each printed circuit board 6 also has an assigned spacer screw 4 (the hexagonal socket is represented here). By means of these spacer screws 4, the width of the inlet slot 5 (see FIG. 4) can be varied and adapted to the individual case.

Also shown clearly in FIG. 2 are the precision screws 16 for precisely fixing the position of the printed circuit boards 6 on the base carrier 1, and therefore the position of the photodiodes 8 in relation to each other.

In FIG. 3, X-ray radiation 18 is incident from the left, through the inlet slot 5 (in the front right part, not represented, because of the upper part 2 having been removed), upon the photodiodes 8. The latter extend in the horizontal direction on the perpendicular first part 10 of the printed circuit boards 6. FIG. 4 also shows clearly the flexible printed circuit board foil in the bend region 11 and the horizontally extending second part 12. The spacer screws 4, with their hexagonal sockets, are also clearly visible. Beneath the base body 1 and connected to the latter is a fastening flange 21, for fastening the entire X-ray line detector to a suspension device.

FIG. 4 shows a view of the mounted detector element 20 from a rotated direction as in FIG. 3. The inlet slot 5, which is defined by the distance between the upper part 2 and the lower part 3, is clearly visible here. X-ray radiation 18, starting from the X-ray source, after screening the test object, is thus incident in a fan shape, through this inlet slot, upon the scintillator located behind the inlet slot 5; the energy that is converted there into light is taken up by the photodiodes 8 and converted into electrical signals.

Two further advantages that are achieved by the embodiment example according to the invention are also shown clearly by FIG. 4. The extremely sensitive electronic devices (for example, the multiplexer 14 and the A/D converter 15) are arranged such that they are not directly struck by incident X-ray radiation 18. Moreover, the base carrier 1 also forms a shielding against any possibly occurring scattered or secondary radiation, which results as the X-ray radiation 18 enters through the inlet slot 5 and strikes parts of the printed circuit boards 6, particularly the scintillators. This prevents the occurrence of interferences resulting from X-ray radiation 18 that could strike the electronic components.

Furthermore, the bend of the printed circuit board 6 enables the detector elements 22 to have a flatter structure. By contrast, the rigid printed circuit boards 6 used hitherto in the state of the art necessitate a significantly higher structure. For this, it is necessary to imagine that the bend in the bend region 11 of the printed circuit board 6, which region is designed as a flexible printed circuit board foil, is not present, with the result that the second part 12, extending horizontally in FIG. 4, would also extend vertically on the printed circuit board 6. Consequently, the height of the detector elements 22 would have to be increased significantly. Owing to the flat structure, a distortion in the screening image of the test object is minimized.

Figure 5:
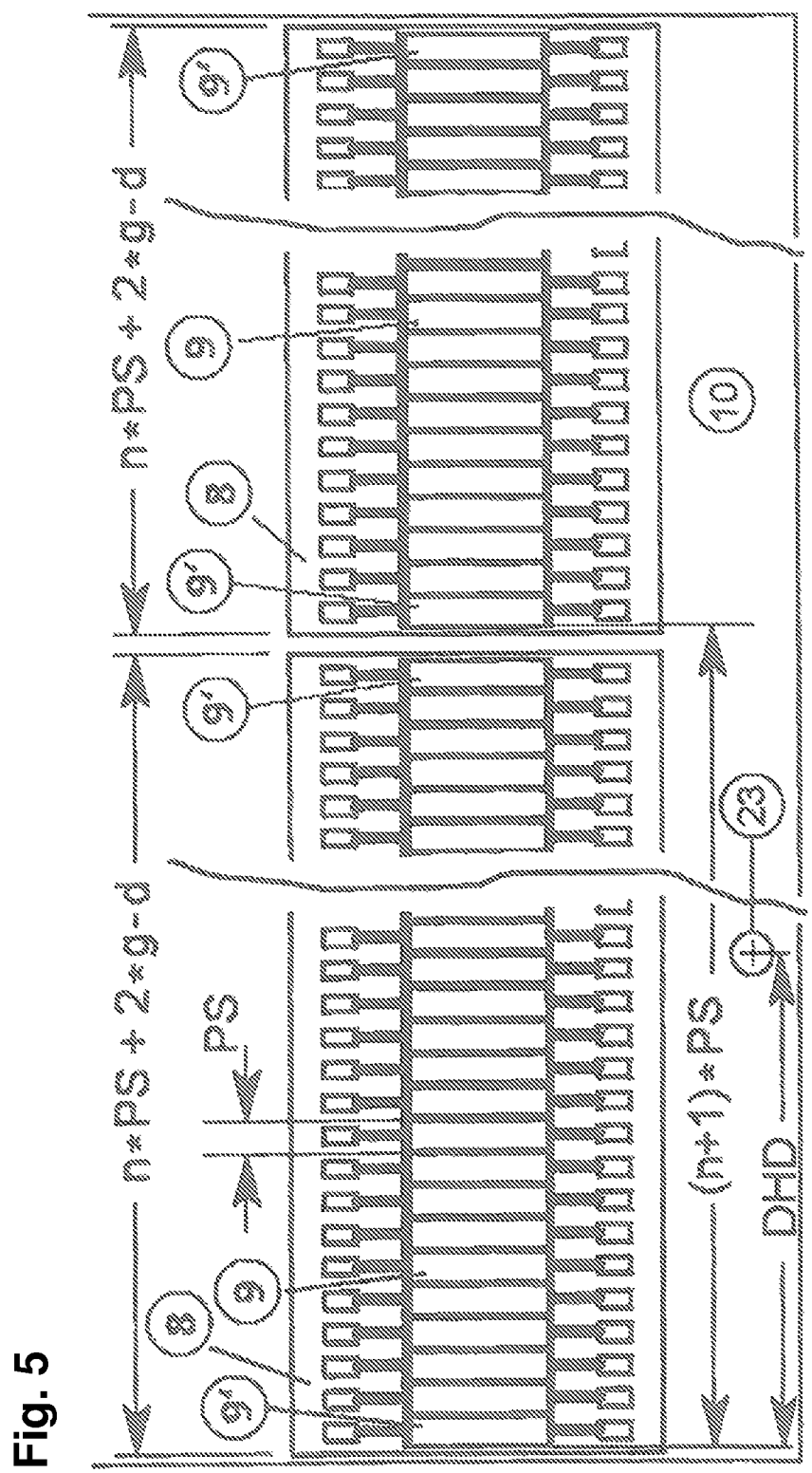
FIG. 5 shows a detail view of a portion of a printed circuit board, in the region of the photodiodes thereof.
Figure 6:
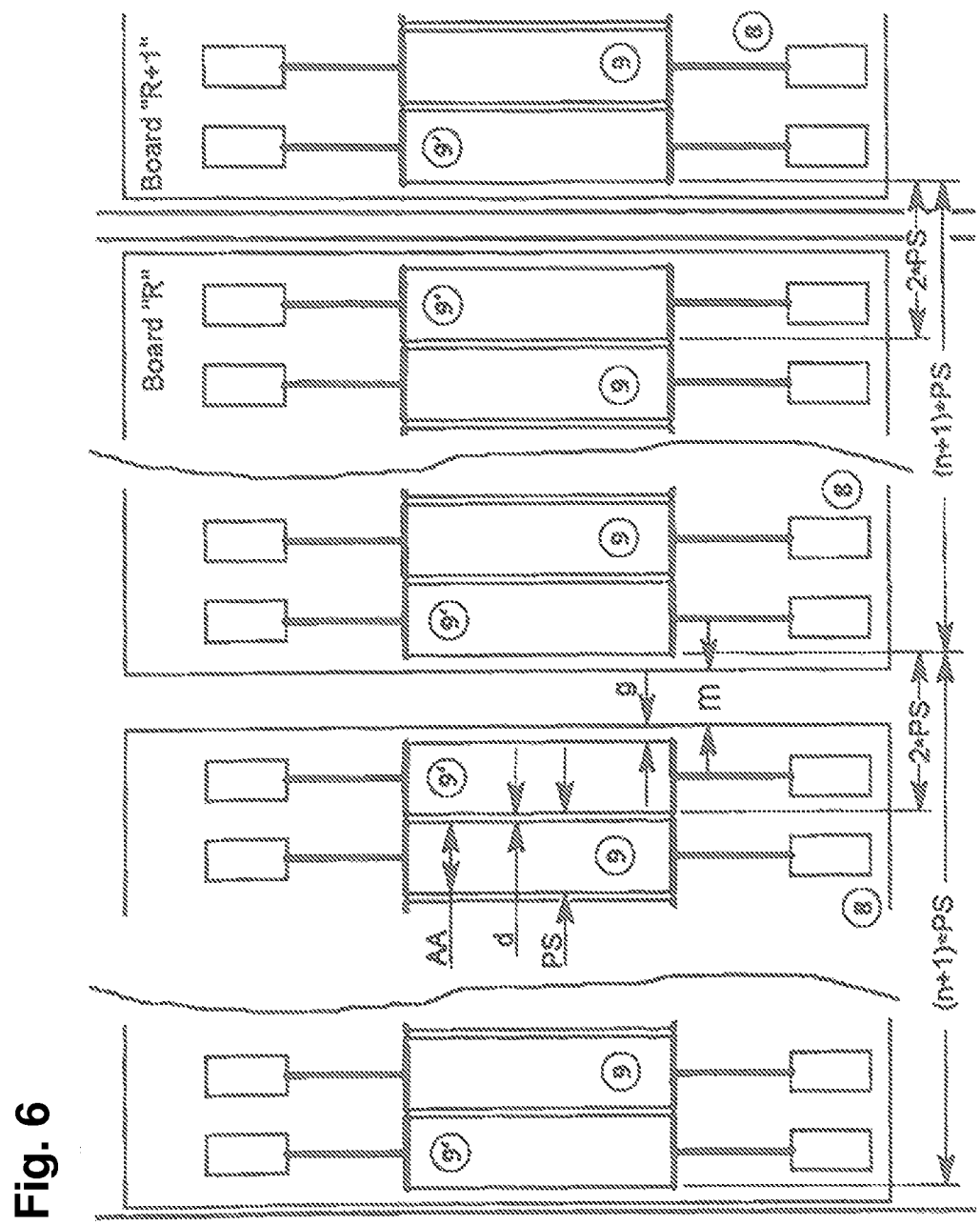
FIG. 6 shows a schematic detail view of an arrangement of three photodiodes on two printed circuit boards.

FIGS. 5 and 6 each show schematic representations of the region of the photodiodes 8. Each photodiode 8 has a number n of pixels 9, 9'. In FIG. 5, two photodiodes 8 are shown on a single printed circuit board 6. FIG. 6 shows, in a much greater enlargement, the spatial relationships both between two photodiodes 8 located on one printed circuit board 6 (left region) and between two abutting end regions of two adjacent printed circuit boards 6 (right region). The active width AA of each individual pixel 9—which is assigned to the active area of a pixel 9—of a photodiode 8 is constant, for example 450 µm. The same also applies to the distances d between two adjacent active areas of the pixels 9 within a photodiode 8. For technical production reasons, the distance g from the active area of the edge pixels 9' to the edge is significantly wider than the distance d between two pixels 9 within the photodiode 8, 100 µm instead of 50 µm in the example in FIG. 6. This results in an effective pixel width PS, termed pixel size, of 500 µm.

This means that, if the two photodiodes 8 were to be abutted against each other on the printed circuit board 6, this would result in a greater distance between the edge pixels 9' than between two inner pixels 9 within a photodiode 8. The result would be that, in the screening image of a tyre, a wire would be represented in an offset manner. In order to prevent this, the two photodiodes 8 are arranged at such a distance apart from each other that the left edge of the active areas of the two edge pixels 9' of adjacent photodiodes 8 corresponds to twice the pixel size PS. If the distance m between the two photodiodes 8 is selected so as to be $$m = PS - 2*g + d,$$

the centre of all pixels 9, 9' is equidistant over the two photodiodes 8.

This results in a design that would correspond exactly to that which would be obtained if one pixel 9 within a photodiode 8 were to be absent. It is therefore possible to refer to a "virtual pixel" between the two photodiodes 8. In the analysis and creation of the screening image, this "virtual pixel" is assigned a greyscale value, which is interpolated from the two edge pixels 9', which are arranged on the left and right of this "virtual pixel". Consequently, the above-mentioned wire in a screening image of a tyre is represented in a continuous manner (unless it is broken), and actual breakage sites can be more easily identified by the operator.

This also applies to the transition of the printed circuit boards 6 in relation to each other (see right side in FIG. 6). For technical production reasons, the photodiodes 8 cannot be mounted so as to be exactly flush with the edge of the printed circuit board 6. In order nevertheless to obtain the pixel equidistance over the entire X-ray line detector, an exact reference point is set on the printed circuit board 6, in relation to the first pixel 9' of the left photodiode 8, designed in the form of the through-hole 23. The hole distance DHD, defined by the distance between the edge pixels 9' of the photodiode 8 and the through-hole 23, is identical on all printed circuit boards 6. Fastening of the printed circuit boards 6 in the fastening hole 17 in the base carrier 1 by means of the precision screw 16 produces the exact distance of the photodiode 8 in relation to the base carrier 1. The fastening holes 17 on the left that are assigned to a printed circuit board 6 each have a distance of $$(n+1)*(\text{number of photodiodes/printed circuit board})*PS$$

in relation to each other.

Since it is possible to produce very accurately both the through-hole 23, in relation to the photodiode 8, and the fastening hole 17, in relation to the base carrier 1, all pixels 9, 9' of the photodiodes 8 are then arranged equidistantly, since the distance of the centre of the last pixel 9' of the right photodiode 8 of the printed circuit board 6 to the first pixel 9' of the left photodiode 8 of the next printed circuit board 6 now corresponds exactly to twice the effective pixel size PS. The greyscale value of this "virtual pixel" is interpreted from the adjacent pixels, as in the case of the "virtual pixel" within a printed circuit board 6.

The resultant length of a photodiode is $$n*PS + 2*g - d.$$

By means of the precision screws 16, the distance, which is in the range of a few hundredths of a millimeter, is maintained exactly, without the need for adjustment. This is achieved in that a screw having a countersunk head is used as precision screw 16 (see FIG. 9). Owing to its conical shape, this countersunk head, when being screwed into the through-hole 23 of the printed circuit board 6, causes the printed circuit board 6 to be aligned and fixed centrally in relation to the precision screw 6, in a very exact manner, on the base carrier 1. The through-hole 23 in the printed circuit board 6, which is designed as a drilled hole, can be introduced into the printed circuit board 6 with extreme precision in respect of the pixels 9 of the photodiodes 8. The same also applies to the production of the fastening hole 17 in the base carrier 1. Both are in a range of a few µm.

Figure 7:
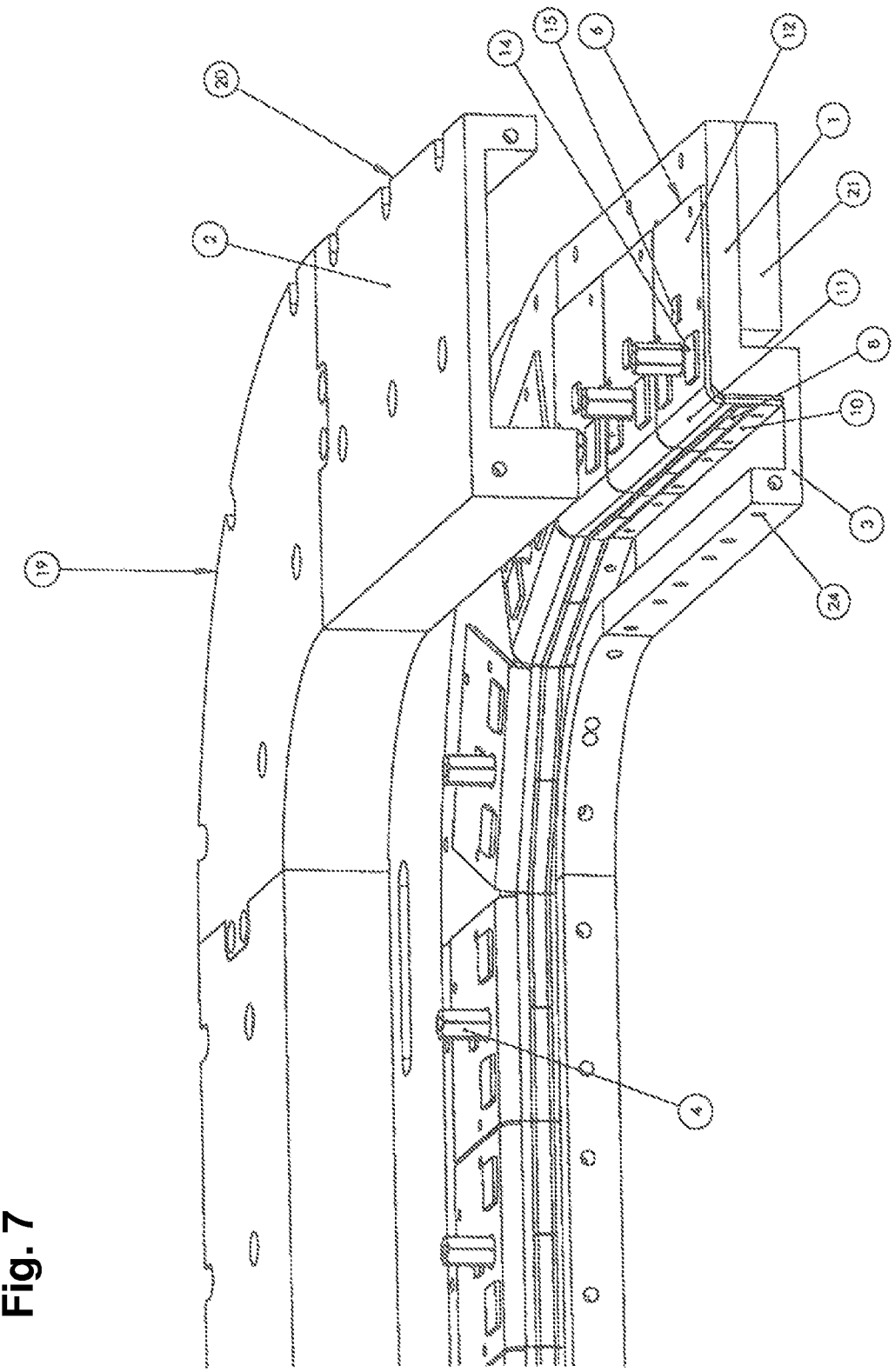
FIG. 7 shows a schematic view as in FIG. 3, with the difference that the lower part and the base carrier form a mechanical unit, and the upper part is not yet mounted.

FIG. 7 shows an embodiment similar to that of FIG. 3, but in which the base carrier 1 and the lower part 3 form a mechanical unit. Here, unlike FIG. 3, the upper part 2 is not yet mounted on the base carrier 1, and the right front upper part 2 is also represented. For production, there is the resultant advantage that a greater precision can be achieved for the inlet slot 5 (see FIG. 4). The disadvantage of this embodiment is that the printed circuit boards 6 must now be differently fastened in the fastening holes 17 on the base carrier 1; this can be effected, for example, by drilled holes 24 on the front side of the shielding in the lower part 3, the precision screws 16 being put through said drilled holes.

Figure 8:
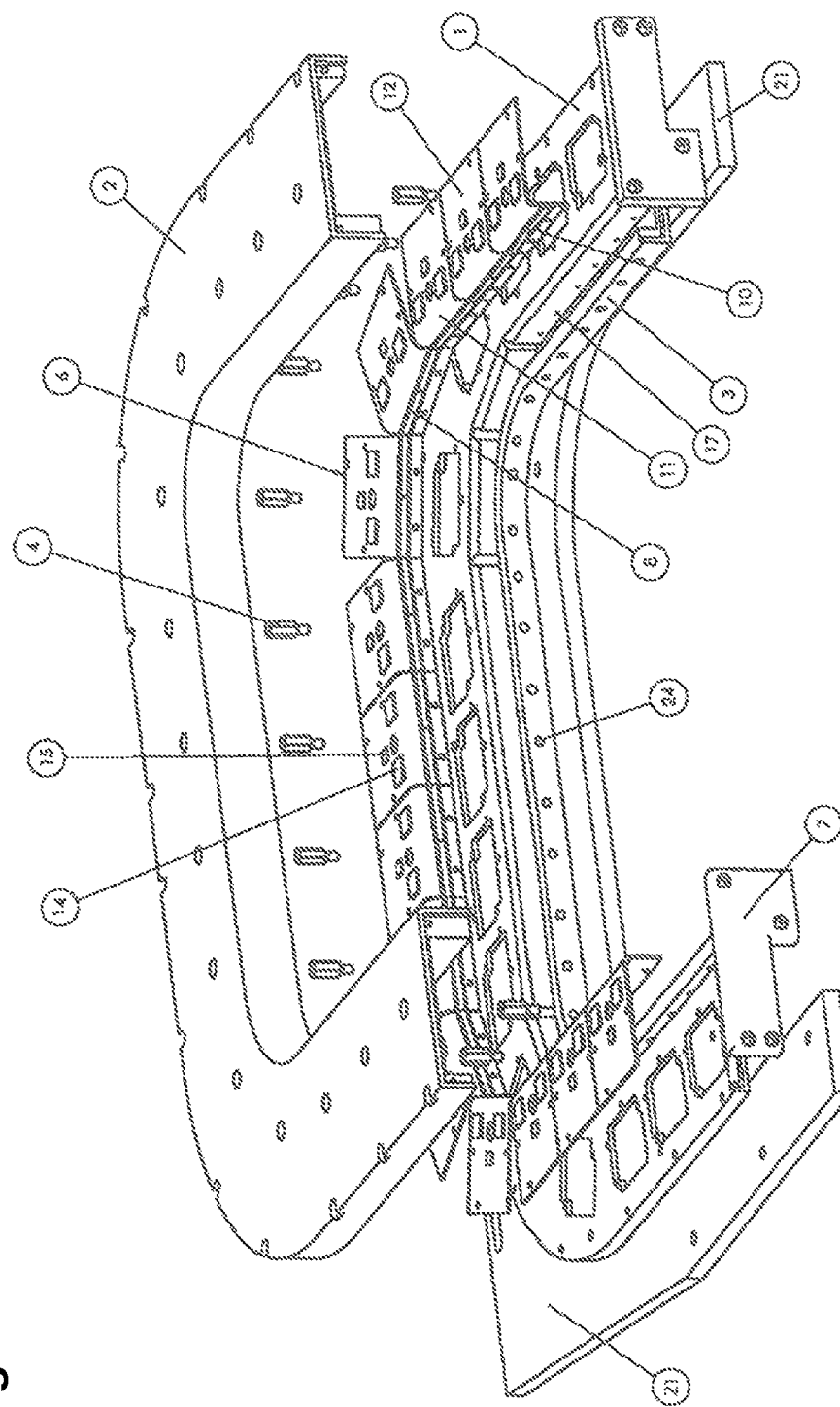
FIG. 8 shows an exploded drawing with the essential elements for an X-ray line detector according to the invention, similar to FIG. 1, with the difference that the modular concept is absent, in place of which the upper part and the lower part, which is formed as one piece with the base carrier, in each case form a mechanical unit.

FIG. 8 shows a modified shape for yet greater precision of the inlet slot 5 (see FIGS. 3 and 4). In this figure, the upper part 2 and the base carrier 1, as well as the lower part 3, are each made of one part. The advantage is that no tolerances arise when the detector elements 20, 19 are being assembled, and consequently the width of the inlet slot 5 does not vary, which would otherwise result in an irregular and possibly distorted image. The disadvantage of this embodiment is that all parts have to fit at their full size into the production machine (milling cutter), and that the modularity is lost.

Figure 9:
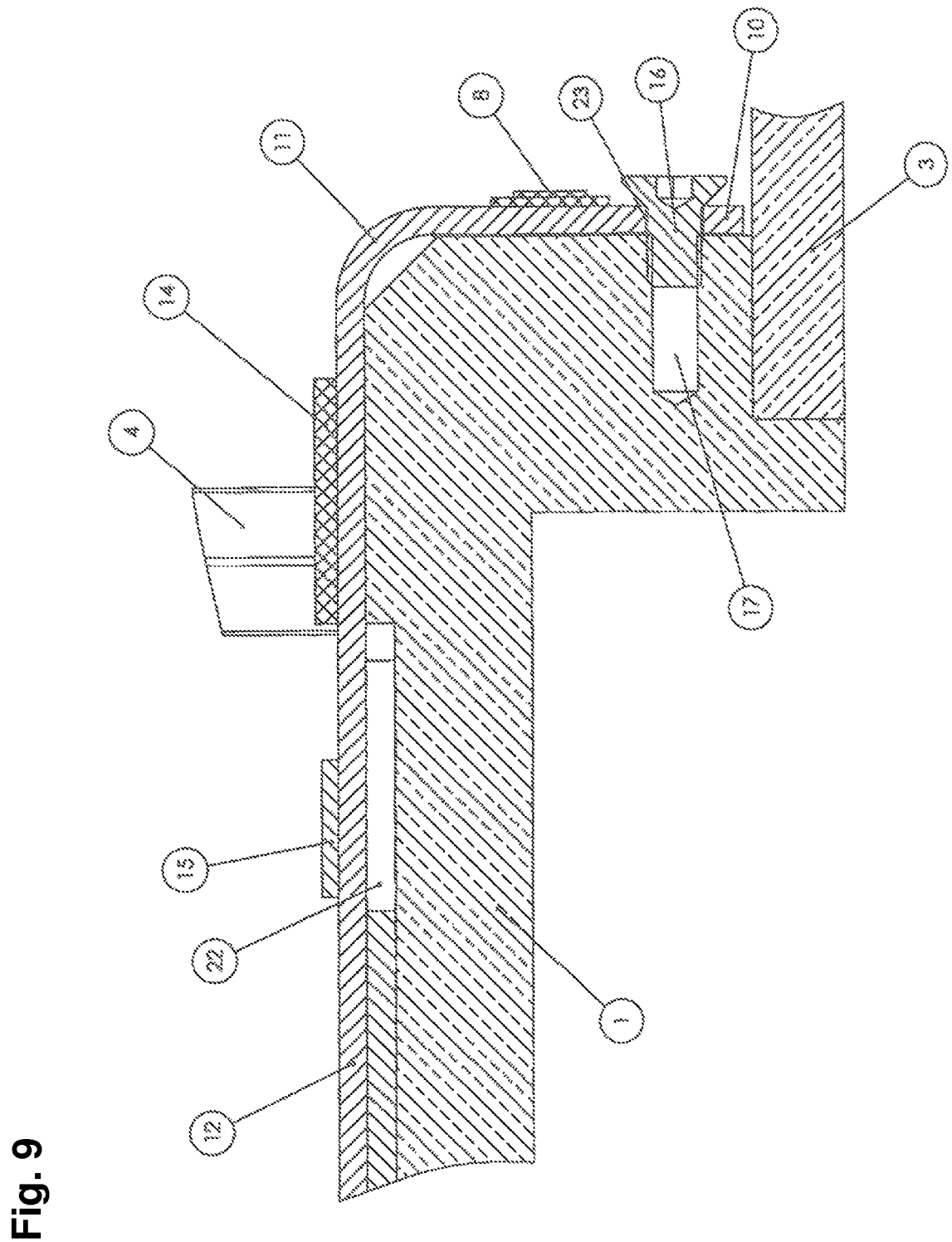
FIG. 9 shows an enlarged portion from FIG. 4, in cross section in the region of the photodiode.

In FIG. 9—as already mentioned above—a cross section through the region of the base carrier 1 with further parts fastened thereto is shown, in which the precision screw 16 is screwed, through the through-hole 23 in the printed circuit board 6, into the fastening hole 17. It can also be clearly seen, at the left upper edge, how an electronic component engages in the opening 22 and is in contact with the base carrier 1. Consequently, a thermal bridge is formed, which results in better dissipation of heat from the electronic component. The further design has already been described at various points above, and is particularly well illustrated here by the enlarged representation, without the need to describe it again.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" should be interpreted as including any singular entity from the listed elements, e.g., A, any subset from the listed elements, e.g., A and B, or the entire list of elements A, B and C.

LIST OF REFERENCES

1 base carrier
2 upper part
3 lower part
4 spacer screw
5 inlet slot
6 printed circuit board
7 end wall
8 photodiode
9 pixel
9' edge pixel
10 first part of the rigid printed circuit board
11 bend region
12 second part of the rigid printed circuit board
13 line wire
14 multiplexer
15 A/D converter
16 precision screw
17 fastening hole
18 X-ray radiation
19 curved detector element
20 straight detector element
21 fastening flange
22 opening
23 through-hole
24 drilled hole
PS effective pixel width (pixel size)
AA width of the active area of a pixel (active area)
d distance of two AAs in relation to each other (distance)
g distance of last AA from photodiode edge (gap)
n number of pixels per photodiode
m distance between two photodiodes
DHD hole distance

What is claimed is:

1. An X-ray line detector comprising:
a housing including an upper part a lower part and a linear inlet slot for X-ray radiation to be detected;
at least one detector element including a plurality of linearly arranged photodiodes disposed opposite the inlet slot, each photodiode being arranged on a printed circuit board mounted on a base carrier disposed in the housing, each photodiode having a multiplicity of pixels including respective active areas of equal width arranged equidistantly in relation to each other with distances between the active areas being equidistant, and adjacent printed circuit boards being spaced apart from each other at a distance such that edge pixels on the respective adjacent printed circuit boards are disposed at a distance from one another corresponding to a sum of the width of the active area of a pixel and twice the distance between adjacent pixels of a photodiode.

2. The X-ray line detector according to claim 1, wherein the upper part of the housing, the lower part of the housing and each base carrier are formed of the same material or of materials having similar thermal coefficients of expansion and similar positions in the electrochemical series, and
wherein each printed circuit board includes a bend region, includes at least one of the respective photodiodes disposed on a first part, and includes line wires starting at the pixels and passing through the respective bend region.

3. The X-ray line detector according to claim 1, wherein attached to each printed circuit board there are in each case at least two photodiodes, wherein the respective distance thereof in relation to each other is selected such that the centre of the last edge pixel of a photodiode is twice the distance of the effective pixel size to the centre of the first edge pixel of the adjoining photodiode.

4. The X-ray line detector according to claim 3, wherein electronic components are arranged, for the purpose of reading out the signals coming from the pixels, such that there is a centre-symmetrical arrangement in relation to the two photodiodes and, consequently, a symmetrical read-out is made possible.

5. The X-ray line detector according to claim 1, wherein, for each photodiode, a multiplexer is arranged on the printed circuit board and this/these multiplexer(s) is/are directly connected to an A/D converter, which is also arranged on the printed circuit board.

6. The X-ray line detector according to claim 1, wherein the analogue components are arranged on one side of the printed circuit board and the digital components are arranged on the other side of the printed circuit board.

7. The X-ray line detector according to claim 1, wherein between each printed circuit board and the base carrier at least one contact region is present as a thermal bridge, preferably one contact region per active analogue component, wherein the base carrier has a material of good thermal conductivity, for example a metal, which is connected to the thermal bridge.

8. The X-ray line detector according to claim 7, wherein the thermal bridge connects an analogue component to the base carrier.

9. The X-ray line detector according to claim 1, wherein arranged between the upper part and the base carrier there is a distance-changing device, in particular spacer screws.

10. The X-ray line detector according to claim 9, wherein the base carrier and the lower part are formed as one piece.

11. The X-ray line detector according to claim 10, wherein suitable apertures, in particular through-holes, or a suitable mounting, are formed in the lower part for the purpose of fastening the printed circuit boards.

12. The X-ray line detector according to claim 7, wherein the upper part and/or the lower part, each taken by itself, is/are formed as one piece over the entire X-ray line detector.

13. The X-ray line detector according to claim 1, wherein each printed circuit board is aligned with high precision in relation to the base body by means of at least one precision screw screwed into a fastening hole in the base body.

14. The X-ray line detector according to claim 1, wherein the distances of the fastening holes in the base body that are respectively assigned to the left through-hole of a printed circuit board follow the formula:

$(n+1)*PS*$(number of photodiodes per printed circuit board).

15. The X-ray line detector according to claim 11, wherein the precision screw has a conically formed screw head.

16. The X-ray line detector according to claim 12, wherein the precision screw engages through a through-hole in the printed circuit board.

17. The X-ray line detector according to claim 1, wherein the line detector has an individually predefinable number of printed circuit boards.

18. The X-ray line detector according to claim 1, wherein all parts consisting of a metal, including precision screws and the spacer screws, consist of the same material or of materials which are close to each other in respect of their coefficients of thermal expansion and their position in the electrochemical series in each case.

19. The X-ray line detector according to claim 1, wherein the detector includes at least two straight detector elements, wherein these detector elements are connected to each other either directly or via curved detector elements, with the result that the X-ray line detector has a rectilinear shape or a U shape.

20. An X-ray line detector comprising:
a housing including an upper part a lower part and a linear inlet slot for X-ray radiation to be detected;
at least one detector element including a plurality of linearly arranged photodiodes disposed opposite the inlet slot, each photodiode being arranged on a printed circuit board mounted on a base carrier disposed in the housing, each photodiode having a multiplicity of pixels of equal width arranged equidistantly in relation to each other with distances between the active areas being equidistant, and adjacent printed circuit boards being spaced apart from each other at a distance such that edge pixels on the respective adjacent printed circuit boards are disposed at a distance from one another corresponding to a sum of the width of the active area of a pixel and twice the distance between adjacent pixels of a photodiode,
wherein the upper part of the housing, the lower part of the housing and each base carrier are formed of the same material or of materials having similar thermal coefficients of expansion and similar positions in the electrochemical series.

21. An X-ray line detector comprising:
a housing including an upper part a lower part and a linear inlet slot for X-ray radiation to be detected;
at least one detector element including a plurality of linearly arranged photodiodes disposed opposite the inlet slot, each photodiode being arranged on a printed circuit board mounted on a base carrier disposed in the housing, each photodiode having a multiplicity of pixels of equal width arranged equidistantly in relation to each other with distances between the active areas being equidistant, and adjacent printed circuit boards being spaced apart from each other at a distance such that edge pixels on the respective adjacent printed circuit boards are disposed at a distance from one another corresponding to a sum of the width of the active area of a pixel and twice the distance between adjacent pixels of a photodiode,
wherein each printed circuit board includes a bend region, includes at least one of the respective photodiodes disposed on a first part, and includes line wires starting at the pixels and passing through the respective bend region.

22. The X-ray line detector according to claim 21, wherein the upper part and the lower part, between which the inlet slot is formed, and the base carrier are spatially matched to each other such that the base carrier serves as a shielding for the second region, which adjoins the bend region and faces away from the first region, against the X-ray radiation which forms as a result of scattering within the detector element (19, 20).

23. The X-ray line detector according to claim 21, wherein the part of the upper part that faces towards the X-ray radiation, in dependence on the material used therefor, is formed so thick that electronic components arranged on the printed circuit board, in a second part of the printed circuit board behind the bend region, are protected against direct X-ray radiation.

* * * * *